United States Patent
Fu et al.

(10) Patent No.: US 11,691,974 B2
(45) Date of Patent: Jul. 4, 2023

(54) 3,9-DIAZASPIRO[5,5]UNDECANE COMPOUND AS FLT3 AND AXL INHIBITORS

(71) Applicant: MEDSHINE DISCOVERY INC., Jiangsu (CN)

(72) Inventors: Xiangyu Fu, Shanghai (CN); Charles Z. Ding, Shanghai (CN); Lihong Hu, Shanghai (CN); Jianyu Lu, Shanghai (CN); Wen Jiang, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 164 days.

(21) Appl. No.: 17/281,479

(22) PCT Filed: Sep. 27, 2019

(86) PCT No.: PCT/CN2019/108522
§ 371 (c)(1),
(2) Date: Mar. 30, 2021

(87) PCT Pub. No.: WO2020/063856
PCT Pub. Date: Apr. 2, 2020

(65) Prior Publication Data
US 2021/0395252 A1    Dec. 23, 2021

(30) Foreign Application Priority Data

Sep. 30, 2018  (CN) .......................... 201811157842.2
Mar. 14, 2019  (CN) .......................... 201910193150.1

(51) Int. Cl.
*C07D 405/14*    (2006.01)
*A61K 31/497*    (2006.01)
*C07D 471/10*    (2006.01)
*A61P 35/02*    (2006.01)

(52) U.S. Cl.
CPC ............ *C07D 471/10* (2013.01); *A61P 35/02* (2018.01)

(58) Field of Classification Search
CPC ................ C07D 405/14; C07D 241/06; A61K 31/497; A61P 35/00; A61P 35/02
USPC ............................. 544/407, 230; 514/255.05
See application file for complete search history.

(56) References Cited

FOREIGN PATENT DOCUMENTS

| CN | 109384774 A | 2/2019 |
|---|---|---|
| JP | 2016-515537 A | 5/2016 |
| WO | WO 2010/128659 A1 | 11/2010 |
| WO | WO 2012/053606 A1 | 4/2012 |
| WO | WO 2013/108754 A1 | 7/2013 |

*Primary Examiner* — Charanjit Aulakh
(74) *Attorney, Agent, or Firm* — McDermott Will & Emery LLP

(57) ABSTRACT

Disclosed in the present invention is a novel compound as FLT3 and AXL inhibitors. Specifically, disclosed are a compound represented by formula (I) and a pharmacologically acceptable salt thereof. (I)

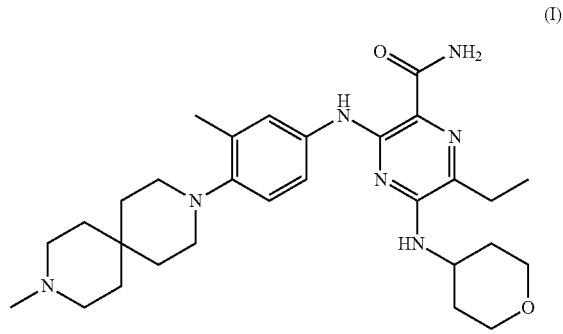

7 Claims, No Drawings

3,9-DIAZASPIRO[5,5]UNDECANE COMPOUND AS FLT3 AND AXL INHIBITORS

RELATED APPLICATIONS

The present application is a United States National Phase under 35 U.S.C. § 371 of International Application No. PCT/CN2019/108522, filed on Sep. 27, 2019, which claims priority to the following Chinese patent applications: CN201811157842.2, filed on Sep. 30, 2018; and CN201910193150.1, filed on Mar. 14, 2019.

FIELD OF THE INVENTION

The present disclosure relates to a class of compounds as FLT3 and AXL inhibitors, and specifically discloses a compound represented by formula (I) and a pharmaceutically acceptable salt thereof and use thereof in the manufacture of a medicament for treatment of AML.

BACKGROUND OF THE INVENTION

Acute myeloid leukemia (AML) is the most common acute leukemia in adults and is a disease caused by the malignant proliferation of bone marrow hematopoietic cells. The incidence of AML is 3.4 per 100,000, and the median age of patients is 67 years. At present, the treatment of AML still needs to rely on chemotherapy, and about 70% of patients who have been relieved eventually relapse and become refractory leukemia. In addition, the prognosis of AML is poor, especially for elderly patients and patients with poor physical fitness. Drug resistance is the most important reason for the failure of treatment of AML, but the mechanism of drug resistance in leukemia is still unknown. Therefore, finding new targets and their inhibitors is of great significance for improving the therapeutic effect of AML and changing the prognosis.

The FLT3 receptor is a member of the type III receptor tyrosine kinase family. FLT3 mutations are the most common genetic mutations in AML, mainly including internal tandem duplication (ITD) mutations in the juxtamembrane domain and point mutations (TKD) at the loop of FLT3. These mutations cause the downstream signaling pathway to be continuously activated, and the mutant cells to proliferate excessively. At present, FLT3 has been considered as an important target for the treatment of AML, and FLT3 inhibitors are also considered to be the most promising molecular targeted drugs for the treatment of AML.

AXL is also known as Ufo, Ark or Tyrol. Its abnormal expression can activate antagonism of tumor cell apoptosis, promote invasion and metastasis of tumor cells, and promote tumor angiogenesis, all of which drive the occurrence and development of tumors. High expression of AXL will cause reduced survival and worse prognosis for patients with AML. In addition, the overexpression of AXL is closely related to the drug resistance of targeted drugs and chemotherapeutic drugs. Recently, AXL has also been found to have potential in immunotherapy. Therefore, the development of dual inhibitors of FLT3 and AXL is expected to achieve better efficacy in the treatment of AML.

WO2012053606A1 reports Compound A (Example 176 in WO2012053606A1), mentioning that such type of molecules has FLT3 inhibitory activity and can be used for the treatment of AML, but no specific test data is given therein.

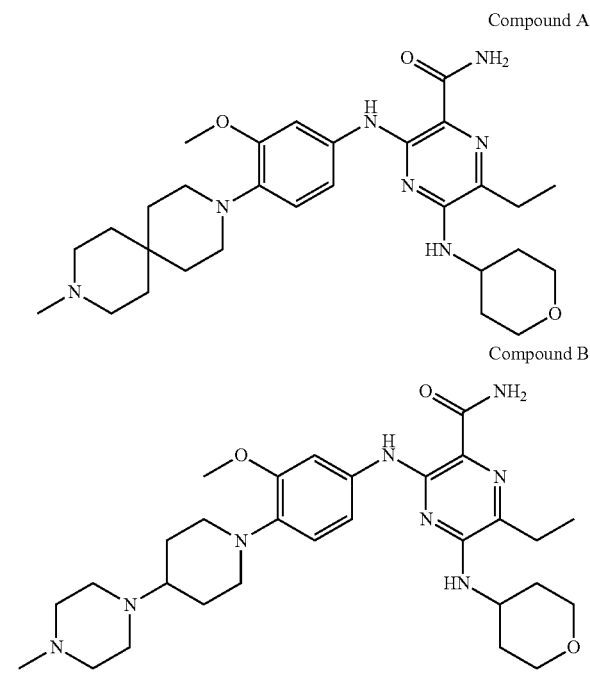

Compound A

Compound B

WO2010128659A1 reports Compound B with FLT3 inhibitory activity (Example 547 in WO2010128659A1). Phase III clinical trials of this compound for the treatment of relapsed or refractory AML are underway.

SUMMARY OF THE INVENTION

Provided herein is a compound represented by formula (I) or a pharmaceutically acceptable salt thereof,

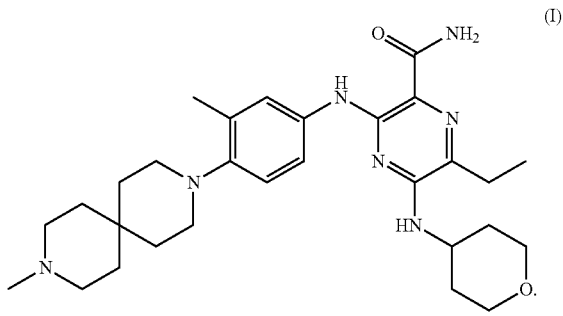 [SMILES: CCc1nc(C(N)=O)c(Nc2ccc(N3CCC4(CCN(C)CC4)CC3)c(C)c2)nc1NC1CCOCC1]

(I)

Also provided herein is the use of the compound represented by formula (I) or a pharmaceutically acceptable salt thereof in the manufacture of medicament for treating cancer.

In some embodiments of the present disclosure, the aforementioned cancer refers to acute myeloid leukemia.

Technical Effect

Provided herein is a novel FLT3/AXL dual inhibitor. Compared with the prior inhibitors, the inhibitor has unexpectedly higher in vitro enzyme activity and cell activity. Especially, the inhibitor has significant advantages in the enzyme activity test for FLT3 mutation. The pharmacokinetic properties of the inhibitor are better than that of the prior inhibitors. In the in vivo assay for MV4-11, a low dose of the compound disclosed herein shows a good tumor inhibitory activity. The drug withdrawal-rebound assay proves that the compound disclosed herein has strong sustained tumor inhibitory ability. In the in vivo assay for Molm-13, the compound disclosed herein shows unexpectedly excellent tumor inhibitory effect, which is obviously better than that of the prior compounds.

Definition and Term

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, without excessive toxicity, irritation, allergic reaction or other problems or complications, commensurate with a reasonable benefit/risk ratio.

The term "pharmaceutically acceptable salt" refers to a salt of the compound disclosed herein that is prepared by reacting the compound having a specific substituent disclosed herein with a relatively non-toxic acid or base. When the compound disclosed herein contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound disclosed herein contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

The present disclosure employs the following abbreviations: aq represents water; HATU represents O-(7-azabenzotriazol-1-yl)-N,N,N',N'-tetramethyluronium hexafluorophosphate; EDC represents N-(3-dimethylaminopropyl)-N'-ethylcarbodiimide hydrochloride; m-CPBA represents 3-chloroperoxybenzoic acid; eq represents equivalent or equivalence; CDI represents carbonyl diimidazole; DCM represents dichloromethane; PE represents petroleum ether; DIAD represents diisopropyl azodicarboxylate; DMF represents N,N-dimethylformamide; DMSO represents dimethyl sulfoxide; EtOAc represents ethyl acetate; EtOH represents ethanol; MeOH represents methanol; CBz represents benzyloxycarbonyl, which is an amino protecting group; BOC represents tert-butoxycarbonyl, which is an amino protecting group; HOAc represents acetic acid; NaCNBH$_3$ represents sodium cyanoborohydride; r.t. represents mom temperature; O/N represents overnight; THF represents tetrahydrofuran; Boc$_2$O represents di-tert-butyldicarbonate; TFA represents trifluoroacetic acid; DIPEA represents diisopropylethylamine; SOCl$_2$ represents thionyl chloride; CS$_2$ represents carbon disulfide; TsOH represents p-toluenesulfonic acid; NFSI represents N-fluoro-N-(phenylsulfonyl)benzenesulfonamide; NCS represents 1-chloropyrrolidine-2,5-dione; n-Bu$_4$NF represents tetrabutylammonium fluoride; iPrOH represents 2-propanol; mp represents melting point; and LDA represents lithium diisopropylamide.

Compounds are named according to the conventional naming principles in the art or by ChemDraw® software, and vendor directory names are used for commercially available compounds.

DETAILED DESCRIPTION OF THE INVENTION

The present disclosure is described in detail below by way of examples, but the examples are not intended to impose any unfavorable limitation on the present disclosure. The compounds of the present disclosure can be prepared by a variety of synthetic methods well known to those skilled in the art, including the specific embodiment listed below, embodiments formed by the specific embodiment listed below in combination with other chemical synthetic methods, and equivalents well known to those skilled in the art. Preferred embodiments include, but are not limited to, the example of the present disclosure. It will be apparent to those skilled in the art that various changes and modifications can be made to the specific embodiments of the present disclosure without departing from the spirit and scope of the present disclosure.

Example 1

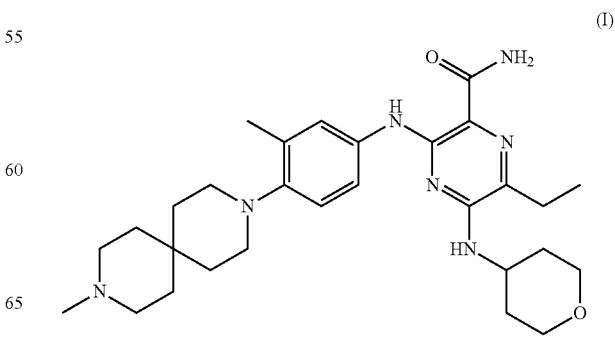

(I)

-continued

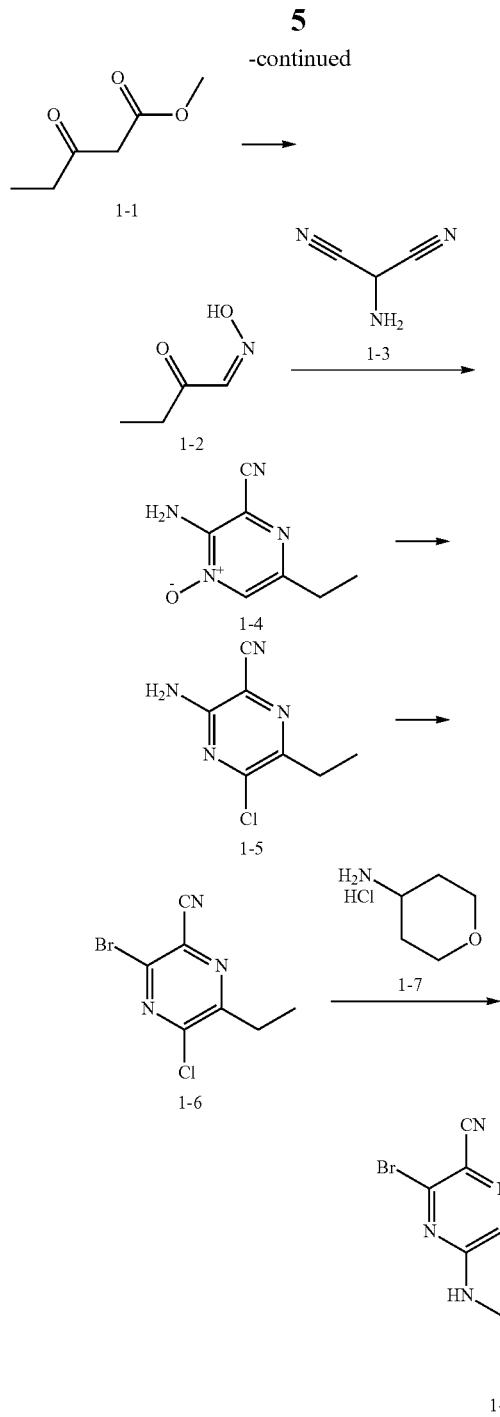

Step A: Compound 1-1 (30 g, 230.52 mmol, 28.57 mL, 1 equiv) was added to water (600 mL), and sodium hydroxide (11.99 g, 299.67 mmol, 1.3 equiv) was then added. The mixture was stirred at 20° C. for 16 hours. The system was cooled to 0° C. to 5° C., and a solution of sodium nitrite (17.50 g, 253.57 mmol, 1.1 equiv) in water (60 mL) was then slowly added. The system was adjusted to a pH of 4 with sulfuric acid, and then further stirred at 20° C. for 12 hours. The aqueous phase was extracted with ethyl acetate (400 mL×2). The organic phases were combined, washed with saturated brine (100 mL×2), dried over sodium sulfate, and concentrated to give compound 1-2. $^1$H NMR (400 MHz, CDCl$_3$) δ=8.83-8.54 (m, 1H), 7.56 (s, 1H), 2.80 (q, J=7.2 Hz, 2H), 1.13 (t, J=7.2 Hz, 3H).

Step B: Compound 1-2 (20 g, 197.82 mmol, 1 equiv) was dissolved in isopropanol (400 mL), and then compound 1-3 (50 g, 197.41 mmol, 0.998 equiv, p-toluenesulfonate) was added. The mixed system was stirred at 20° C. for 16 hours. The reaction solution was poured into water (300 mL), and extracted with ethyl acetate (500 mL×3). The organic phases were combined, washed with saturated brine (800 mL), dried over sodium sulfate, and concentrated to give compound 1-4. MS (ESI) m/z: 165.3 [M+H$^+$].

Step C: Compound 1-4 (31 g, 188.84 mmol, 1 equiv) was dissolved in N,N-dimethylformamide (300 mL) and cooled to 0° C. Phosphorus oxychloride (78.52 g, 512.09 mmol, 47.59 mL, 2.71 equiv) was then slowly added dropwise while keeping the temperature below 5° C. After the addition was completed, the system was heated to 80° C. and stirred for 2 hours. The reaction solution was added dropwise to ice (900 g), allowed to warm to 20° C., and then stirred for 16 hours. Solid was precipitated out and filtered. The filter cake was collected and dried under vacuum to give compound 1-5.

Step D: Tert-butyl nitrite (20.61 g, 199.88 mmol, 23.77 mL, 2.5 equiv) and CuBr$_2$ (21.43 g, 95.94 mmol, 4.49 mL, 1.2 equiv) were dissolved in N,N-dimethyl formamide (200 mL), and the system was heated to 65° C. A solution of compound 1-5 (14.6 g, 79.95 mmol, 1 equiv) in N,N-dimethylformamide (150 mL) was then added dropwise. The reaction solution was reacted at 65° C. for 0.5 hours, and then poured into ice water (1000 g). The precipitated solid was filtered. The filter cake was dissolved in ethyl acetate (300 ml) and filtered again. The filtrate was concentrated to give compound 1-6. $^1$H NMR (400 MHz, DMSO-d$_6$) δ=2.92 (q, J=7.2 Hz, 2H), 1.23 (t, J=7.2 Hz, 3H).

Step E: Compound 1-6 (4 g, 16.23 mmol, 1 equiv) and compound 1-7 (1.97 g, 14.31 mmol, 0.882 equiv) were dissolved in 1,4-dioxane (50 mL), and then N,N-diisopropylethylamine (5.03 g, 38.95 mmol, 6.78 mL, 2.4 equiv) was added. The mixture was heated to 65° C. and stirred for 12 hours. Water (100 ml) was poured into the reaction solution, and the mixture was stirred at 20° C. for 0.5 hour. The mixture was filtered. The filter cake was washed with water, and dried under vacuum to give compound 1-8. MS (ESI) m/z: 310.9, 312.9 [M+H$^+$].

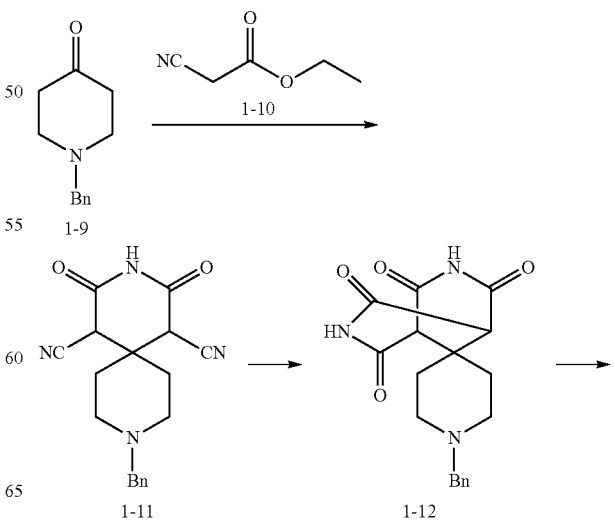

-continued

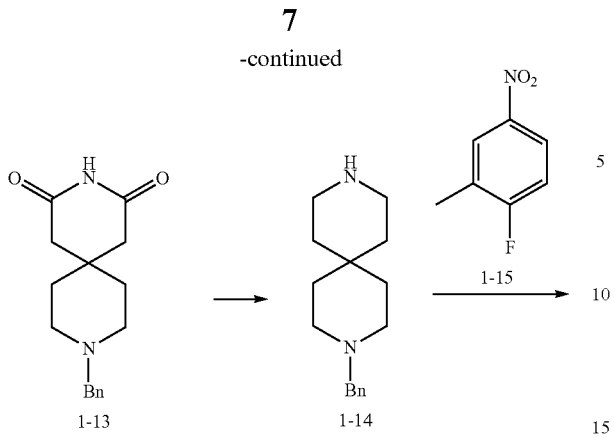

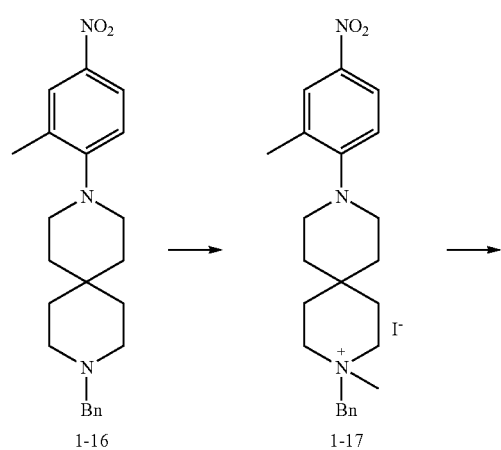

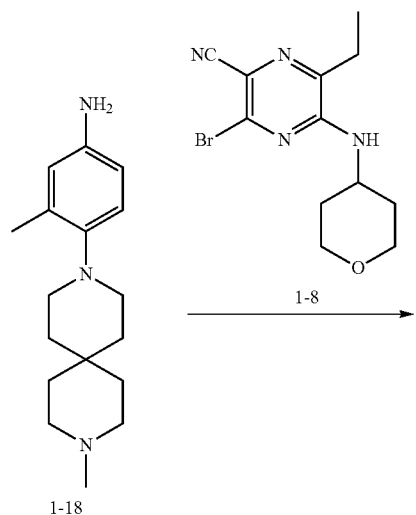

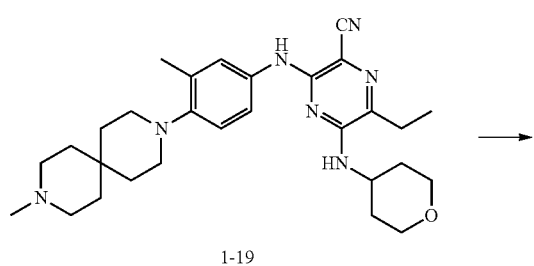

-continued

Step F: Ammonium acetate (2.04 g, 26.42 mmol, 0.1 equiv) was added to a solution of compound 1-10 (89.65 g, 792.59 mmol, 84.58 mL, 3 equiv) in methanol (100 mL) at 5° C. to 8° C., and then compound 1-9 (50 g, 264.20 mmol, 49.02 mL, 1 equiv) was added. Ammonia water (51.85 g, 369.87 mmol, 56.98 mL, 25%, 1.4 equiv) was then added to the mixed solution below 10° C. The mixed solution was stirred at 0° C. to 5° C. for 1 hour. The reaction mixture was then warmed to 20° C. and stirred for 20 hours. Water (100 ml) was added to the system and the mixture was heated to 55° C. The reaction solution was adjusted to a pH of 4 with hydrochloric acid (12 mol/L) while keeping the temperature not to exceed 70° C. Thereafter, the mixture was cooled to 10° C., stirred for 30 minutes, and then filtered. The filter cake was washed with water and dried under reduced pressure to give compound 1-11. MS (ESI) m/z: 323.1 [M+H$^+$].

Step G: To a mixture of sulfuric acid (161.92 g, 1.65 mol, 88 mL, 10.65 equiv) and water (12.00 g, 666.10 mmol, 12 mL, 4.30 equiv) was added compound 1-11 (49.95 g, 154.95 mmol, 1 equiv). At this time, the temperature of the mixture was raised to 40° C. The mixture was then heated to 80° C. and stirred for 2 hours. Water (20.00 g, 1.11 mol, 20 mL, 7.16 equiv) was then added. The mixture was heated to 100° C. and stirred for 1.5 hours. Water (250 ml) was added to the reaction solution and the mixture was stirred at 30° C. for 12 hours. The reaction solution was then filtered. The filter cake was washed with water, and dried under reduced pressure to give compound 1-12. MS (ESI) m/z: 342.0 [M+H$^+$].

Step H: To an aqueous solution of sodium hydroxide (5 mol/L, 183.45 mL, 8 equiv) was added compound 1-12 (39.14 g, 114.66 mmol, 1 equiv). The mixture was heated to 80° C. and stirred for 2 hours. The system was cooled to 60° C., and hydrochloric acid (12 mol/L, 75 ml, 7.85 equiv) was slowly added. The system was heated to 75° C. and hydrochloric acid (12 mol/L, 15 ml, 1.57 equiv) was added dropwise. The mixture was heated to 85° C. and stirred for 1 hour. The mixture was then cooled to 25° C. and stirred for 16 hours. Water (200 ml) was added to the reaction solution. The mixture was cooled to 10° C., and filtered. The filter cake was washed with water (300 ml) and dried under reduced pressure to give compound 1-13. MS (ESI) m/z: 273.1 [M+H$^+$].

Step I: Compound 1-13 (28 g, 102.81 mmol, 1 equiv) was dissolved in tetrahydrofuran (300 mL). The mixture was heated to 70° C., and lithium tetrahydroaluminum (15.61 g, 411.25 mmol, 4 equiv) was then added in portions to the solution. The mixture was stirred at 70° C. for 12 hours. After cooled to room temperature, a saturated sodium sulfate solution (30 mL) was slowly added dropwise to the reaction solution, and the mixture was then filtered. The filter cake was washed with ethyl acetate (100 mL). The filtrates were combined and concentrated to give compound 1-14. MS (ESI) m/z: 245.1 [M+H$^+$].

Step J: Compound 1-14 (0.5 g, 2.05 mmol, 1 equiv) and compound 1-15 (317.39 mg, 2.05 mmol, 1 equiv) were dissolved in N,N-dimethylformamide (10 mL), and potassium carbonate (565.55 mg, 4.09 mmol, 2 equiv) was added. The mixture was heated to 80° C. and stirred for 12 hours. The reaction solution was poured into water (60 mL), and extracted with ethyl acetate (60 mL×2). The organic phases were combined, washed with saturated brine (60 mL), dried and concentrated to give compound 1-16. MS (ESI) m/z: 380.0 [M+H$^+$].

Step K: To a solution of compound 1-16 (550 mg, 1.45 mmol, 1 equiv) in dichloromethane (15 mL) was added methyl iodide (246.85 mg, 1.74 mmol, 108.27 μL, 1.2 equiv), and the mixture was stirred at 25° C. for 12 hours. The reaction solution was concentrated to give compound 1-17. MS (ESI) m/z: 394.1 [M+H$^+$].

Step L: To a solution of compound 1-17 (620 mg, 1.19 mmol, 1 equiv) in ethanol (20 mL) was added wet palladium carbon (100 mg, 10%). The mixture was purged with hydrogen, and then heated to 60° C. The mixture was stirred under hydrogen pressure of 50 psi for 12 hours. The reaction solution was then filtered and the filtrate was concentrated to give compound 1-18. MS (ESI) m/z: 274.1 [M+H$^+$].

Step M: To a solution of compound 1-18 (300 mg, 1.10 mmol, 1 equiv) and compound 1-8 (341.43 mg, 1.10 mmol, 1 equiv) in 1,4-dioxane (10 mL) were added palladium acetate (24.63 mg, 109.72 μmol, 0.1 equiv), 4,5-bis(diphenylphosphino)-9,9-dimethylxanthene (63.49 mg, 109.72 μmol, 0.1 equiv) and potassium carbonate (303.29 mg, 2.19 mmol, 2 equiv). The system was purged with nitrogen, then heated to 80° C., and stirred under a nitrogen atmosphere for 12 hours. The reaction solution was filtered, and the filter cake was washed with ethyl acetate (60 ml). The filtrate was concentrated and the resultant crude product was purified to give compound 1-19. MS (ESI) m/z: 504.2 [M+H$^+$].

Step N: Compound 1-19 (200 mg, 397.08 μmol, 1 equiv) was dissolved in dimethyl sulfoxide (2 mL) and ethanol (6 mL), and the system was cooled to 0° C. Sodium hydroxide (4 mol/L, 297.81 μL, 3 equiv) and hydrogen peroxide (135.06 mg, 1.19 mmol, 114.46 μL, 30% pure, 3 equiv) was then added. The reaction solution was allowed to warm to 25° C. and stirred for 12 hours.

Method 1: The reaction solution was poured into water (30 ml) and extracted with ethyl acetate (40 ml×3). The organic phases were combined, washed with saturated brine (40 ml), dried over sodium sulfate, and concentrated to give the crude product, which was then separated and purified (Preparative high performance liquid chromatography, column: Phenomenex Synergi C18 150*25*10 microns; mobile phase: [water (0.1% trifluoroacetic acid)-acetonitrile]; acetonitrile %: 10%-37%, 10 minutes) to give the trifluoroacetate salt of the compound of formula (I). $^1$H NMR (400 MHz, DMSO-d$_6$) δ=11.13 (s, 1H), 9.23 (br s, 1H), 7.61-7.40 (m, 3H), 7.28-7.11 (m, 2H), 6.85 (d, J=7.2 Hz, 1H), 4.18-4.06 (m, 1H), 3.99-3.91 (m, 2H), 3.41-3.37 (m, 2H), 3.30-3.27 (m, 2H), 3.13-2.91 (m, 6H), 2.79 (d, J=4.4 Hz, 3H), 2.62-2.55 (m, 2H), 2.33-2.28 (m, 3H), 2.03-1.78 (m, 6H), 1.73-1.44 (m, 6H), 1.19 (t, J=7.2 Hz, 3H). MS (ESI) m/z: 522.0 [M+H$^+$].

Method 2: Water (20 ml) was added to the reaction solution and stirred for 30 minutes. The mixture was filtered, and the filter cake was washed with water (10 ml). The filter cake was slurried with ethanol (5 ml), filtered, and dried under reduced pressure to give the compound of formula (I). $^1$H NMR (400 MHz, DMSO-d$_6$) δ=11.01 (s, 1H), 7.52 (d, J=2.8 Hz, 1H), 7.43 (d, J=2.4 Hz, 1H), 7.36 (dd, J=8.8 Hz, 2.4 Hz, 1H), 7.20 (d, J=2.4 Hz, 1H), 6.99 (d, J=8.8 Hz, 1H), 6.79 (d, J=7.6 Hz, 1H), 4.15-4.06 (m, 1H), 3.95-3.92 (m, 2H), 3.42-3.39 (m, 2H), 2.74-2.71 (m, 4H), 2.56 (q, J=7.6 Hz, 2H), 2.28-2.25 (m, 4H), 2.22 (s, 3H), 2.14 (s, 3H), 1.88-1.84 (m, 2H), 1.69-1.45 (m, 10H), 1.18 (t, J=7.2 Hz, 3H). MS (ESI) m/z: 522.3 [M+H$^+$].

Assay Example 1: Assay of FLT3 Inhibitory Activity In Vitro

Assay Materials:
FLT3 Kinase Enzyme System (kinase system) was purchased from Promega. Envision Multi-Label Analyzer (PerkinElmer).

Assay Method:
The enzyme, substrate, ATP (adenosine triphosphate) and inhibitors were diluted using the buffer solution in the kit.

The compounds to be tested were 5-fold serially diluted with a pipette to obtain eight concentrations, i.e., from 5 μmol/L to 0.065 nmol/L, and the final concentration of dimethyl sulfoxide was 5%. The assay was carried out in duplicate. 1 μl of the inhibitors of each concentration gradient, 2 μl of the FLT3 enzyme (15 ng), and a 2 μl mixture of the substrate and ATP (50 μmol/L ATP, 0.1 μg/μL MBP) were added to the microplate. At this time, the final concentration gradient of the compounds was from 1 μmol/L to 0.013 nmol/L. The system was reacted at 30° C. for 120 minutes. After the reaction was completed, 5 μL. of ADP-Glo reagent was added to each well. The system was further reacted at 30° C. for 40 minutes. After the reaction was completed, 10 μL. of kinase detection reagent was added to each well and reacted at 30° C. for 30 minutes. The chemiluminescence was then read by the PerkinElmer Envision multi-label analyzer with an integration time of 0.5 seconds.

Data Analysis:
The original data was converted into an inhibition rate, and the IC$_{50}$ value can be obtained by four-parameter curve fitting. The inhibitory activity of the compound of the present disclosure on FLT3 enzyme was provided in Table 1.

Assay results: see Table 1.

Conclusion

The compound of the present disclosure has excellent in vitro inhibitory activity against FLT3.

TABLE 1

| Sample | FLT3 IC$_{50}$ (nmol/L) |
|---|---|
| Trifluoroacetate salt of compound A | 4.02 |
| Compound B | 0.81 |
| Trifluoroacetate salt of compound of formula (I) | 0.42 |

Assay Example 2: Assay of AXL Inhibitory Activity In Vitro

Assay Materials:
AXL Kinase Enzyme System (kinase system) was purchased from Promega. Envision multi-label Analyzer (PerkinElmer).

Assay Method:
The enzyme, substrate, ATP and inhibitors were diluted using the buffer solution in the kit.

The compounds to be tested were 5-fold serially diluted with a pipette to obtain eight concentrations, i.e., from 5 µmol/L to 0.065 nmol/L, and the final concentration of dimethyl sulfoxide was 5%. The assay was carried out in duplicate. 1 µl of the inhibitors of each concentration gradient, 2 µl of the AXL enzyme (6 ng), and a 2 µl mixture of the substrate and ATP (50 µmon ATP, 0.2 µg/µL Axltide) were added to the microplate. At this time, the final concentration gradient of the compounds was from 1 µmol/L to 0.013 nmol/L. The system was reacted at 30° C. for 60 minutes. After the reaction was completed, 5 µL of ADP-Glo reagent was added to each well. The system was further reacted at 30° C. for 40 minutes. After the reaction was completed, 10 µL of kinase detection reagent was added to each well and reacted at 30° C. for 30 minutes. The chemiluminescence was then read by the PerkinElmer Envision multi-label analyzer with an integration time of 0.5 seconds.

Data Analysis:

The original data was converted into an inhibition rate, and the $IC_{50}$ value can be obtained by four-parameter curve fitting. The inhibitory activity of the compound of the present disclosure on AXL enzyme was provided in Table 2.

Assay results: see Table 2.

Conclusion

The compound of the present disclosure has excellent in vitro inhibitory activity against AXL.

TABLE 2

| Sample | AXL $IC_{50}$ (nmol/L) |
| --- | --- |
| Trifluoro acetate salt of the compound A | 5.76 |
| Compound B | 1.37 |
| Trifluoroacetate salt of compound of formula (I) | 1.22 |

Assay Example 3: Assay of Inhibiting Proliferation of FLT3 Mutantin Vitro

Assay Method:

The assay was carried out using KINOMEscan™ technology. The assay compounds were stored in 100% DMSO. The assay was carried out by means of 3-fold dilution and 11-point fitting. All compounds used for Kd determination were dispersed by ultrasound, then directly diluted and tested. All reactions were carried out in a 384-well polypropylene plate. Each portion has a final volume of 0.02 ml. The plate was incubated with shaking at room temperature for 1 hour, and then processed. The kinase concentration in the eluent was finally determined by qPCR method. Kd was obtained by fitting.

Assay results: see Table 3.

TABLE 3

| | Kd(nmol/L) | |
| --- | --- | --- |
| Target | Compound B | Trifluoroacetate salt of compound of formula (I) |
| FLT3(D835H) | 3.2 | 2.3 |
| FLT3(D835V) | 0.53 | 0.23 |
| FLT3(D835Y) | 1.7 | 1.4 |
| FLT3(ITD) | 5.3 | 3.6 |
| FLT3(ITD, D835V) | 0.41 | 0.2 |

TABLE 3-continued

| | Kd(nmol/L) | |
| --- | --- | --- |
| Target | Compound B | Trifluoroacetate salt of compound of formula (I) |
| FLT3(ITD, F691L) | 0.76 | 0.21 |
| FLT3(K663Q) | 59 | 10 |
| FLT3(N841I) | 8.2 | 5.4 |
| FLT3(R834Q) | 65 | 31 |

Conclusion

The compound of the present disclosure has excellent in vitro inhibitory activity against mutant FLT3 targets, which shows higher activity for all 10 mutants than that of the known compound B, wherein the activity for FLT3 (ITD, F691L) is 3.6 times higher and the activity for FLT3 (K663Q) is 5.9 times higher. Such higher activity against mutant FLT3 is of high clinical significance considering that the point mutation is an important cause of drug resistance of FLT3 inhibitors.

Assay Example 4: Assay of Inhibiting Proliferation of MV-4-11 In Vitro

Assay Materials:

IMDM medium, fetal bovine serum, and penicillin/streptomycin antibiotics were purchased from Promega (Madison, Wis.). The MV-4-11 cell line was purchased from the Cell Bank of the Chinese Academy of Sciences. Envision Multi-Label Analyzer (PerkinElmer).

Assay Method:

MV-4-11 cells were seeded in a white 96-well plate with 80 µL of cell suspension per well containing 10,000 MV-4-11 cells. The cell plate was cultured overnight in a carbon dioxide incubator.

The compounds to be tested were 5-fold serially diluted with a pipette to obtain eight concentrations, i.e., from 2 mmol/L to 26 nmol/L. The assay was carried out in duplicate. 78 µL of medium was added to the intermediate plate, and then 2 µL per well of the serially diluted compounds were transferred to the intermediate plate according to the corresponding position. After mixing, an amount of 20 µL per well was transferred to the cell plate. The cell plate was cultured in a carbon dioxide incubator for 3 days.

25 µL per well of Promega CellTiter-Glo reagent was added to the cell plate and incubated at room temperature for 10 minutes to stabilize the luminescence signal. A PerkinElmer Envision multi-label analyzer was used for reading.

Data Analysis:

The original data was converted into an inhibition rate, and the IC50 value can be obtained by four-parameter curve fitting. The inhibitory activity of the compound of the present disclosure on the proliferation of MV-4-11 cells was provided in Table 4.

Assay results: see Table 4.

Conclusion

The compound of the present disclosure has excellent inhibitory activity on the proliferation of MV-4-11 cells.

TABLE 4

| Sample | MV-4-11 IC$_{50}$ (nmol/L) |
| --- | --- |
| Compound A | 5.4 |
| Compound B | 4.65 |
| Trifluoroacetate salt of compound of formula (I) | 3.02 |

Assay Example 5: In Vivo Pharmacokinetic Study in Mice

Assay Purpose:

The purpose of this assay is to evaluate the pharmacokinetic behavior of the compound after single administration by intravenous injection and intragastric gavage, and to investigate the bioavailability after administration by intragastric gavage.

Assay Procedure:

CD-1 male mice aged 7 to 10 weeks were selected. The doses for intravenous and oral administration were 1 mg/kg and 2.5 mg/kg, respectively. The mice were fasted for at least 12 hours before the administration, and resumed feeding 4 hours after the administration. The mice had free access to water throughout the assay period.

On the day of the assay, the animals in the intravenous group were administrated the corresponding compound through a single injection in the tail vein at an administration volume of 5 mL/kg; the oral group were administrated the corresponding compound through a single intragastric gavage at an administration volume of 10 mL/kg. The animals were weighed before administration, and the administration volume was calculated based on the body weight. The time for collecting samples was: 0.083 (the injection group), 0.25, 0.5, 1, 2, 4, 8, 24 h. About 30 μL of whole blood was collected from the saphenous vein at each time point to prepare plasma for concentration determination by high-performance liquid chromatography-tandem mass spectrometry (LC-MS/MS). All animals were euthanized by $CO_2$ anesthesia after collecting the PK samples at the last time point. The plasma concentrations were processed by non-compartmental model of WinNonlin™ Version 6.3 (Pharsight, Mountain View, Calif.) pharmacokinetic software, and the pharmacokinetic parameters were calculated by the linear logarithm trapezoidal method.

Assay results: The results of in vivo PK property evaluation in mice are shown in Table 5.

Assay Conclusion

The compound of the present disclosure has an appropriate clearance rate, has relatively good oral AUC and bioavailability, and has good pharmacokinetic properties in mice. The compound of the present disclosure has unexpectedly improved PK properties compared to compound A.

TABLE 5

Results of evaluation of in vivo pharmacokinetic properties

| Administration | Parameter | Compound A | Compound B | Trifluoroacetate salt of compound of formula (I) |
| --- | --- | --- | --- | --- |
| Injection (1 mg/kg) | $T_{1/2}$ (hr) | 2.13 | 2.09 | 2.40 |
| | Vdss (L/Kg) | 8.93 | 7.47 | 8.63 |
| | Cl (mL/min/Kg) | 73.4 | 46.7 | 48.5 |
| | $AUC_{0-last}$ (nm·h) | 403 | 605 | 604 |
| Oral administration (2.5 mg/kg) | $C_{max}$ (nM) | 13.4 | 85.3 | 60.5 |
| | $T_{max}$ (h) | 1.00 | 1.00 | 4.00 |
| | $T_{1/2}$ (h) | 7.57 | 5.59 | 4.41 |
| | $AUC_{0-last}$ (nM/hr) | 74.5 | 501 | 598 |
| | F % | 7.39 | 33.1 | 37.3 |

Assay Example 6: Assay of Inhibition of MV4-11 Subcutaneous Xenograft Tumor In Vivo Assay Purpose:

In this assay, the anti-tumor effect of the compounds was evaluated using a nude mice model of subcutaneous xenograft tumor of human biphenotypic B bone marrow mononuclear leukemia cell MV4-11.

Assay Procedure:

Human biphenotypic B bone marrow mononuclear leukemia cell MV4-11 was cultured in vitro in suspension with a RPMI1640 medium supplemented with 10% fetal bovine serum, 100 U/mL penicillin and 100 μg/mL streptomycin in a 5% $CO_2$ cell incubator at 37° C. Routine passaging was performed twice a week. Cells in the logarithmic growth phase were collected, counted and then used for inoculation.

$10 \times 10^6$ MV4-11 cells were inoculated subcutaneously on the back of the right neck of each mouse, wherein the inoculation volume was 0.2 mL, and the cell suspension was PBS plus matrigel (volume ratio 1:1). The assay of efficacy in vivo was performed on the 13th day after the cell inoculation, at which time the average tumor volume reached 181 mm$^3$. The mice were randomly divided into groups with 6 mice in each group, and administration to the mice started.

The diameter of the tumor was measured with vernier calipers twice a week. The formula for calculating the tumor volume is: $V=0.5 \times a \times b^2$, where a and b represent the long and short diameters of the tumor, respectively.

After 14 days of administration, the administration was stopped, and the rebound of the tumor was observed.

Assay Results:

The tumor inhibitory effect of the compounds is shown in Table 6.

TABLE 6

Results of MV4-11 ectopic xenograft assay

| Compound | Blank | Compound A | Compound B | Trifluoroacetate salt of compound of formula (I) |
| --- | --- | --- | --- | --- |
| Dose(mg/kg) | 0 | 20 | 5 | 5 |
| Dosing frequency | Once a day | Once a day | Once a day | Once a day |
| Mode of administration | oral | oral | oral | oral |

TABLE 6-continued

Results of MV4-11 ectopic xenograft assay

| Compound | | Blank | Compound A | Compound B | Trifluoroacetate salt of compound of formula (I) |
|---|---|---|---|---|---|
| Average tumor volume (cubic millimeter) | Day 0 | | | 181 | |
| | Day 14 | 955 | 39 | 41 | 32 |
| % Inhibition rate on day 14 | | — | 118% | 118% | 119% |
| Average tumor volume (cubic millimeter) | Day 25 | 2373 (Euthanasia) | 258 | 320 | 234 |
| | Day 35 | — | 988 | 1279 | 849 |

Assay Conclusion

The compound of the present disclosure has a significant inhibitory effect against the growth of xenograft tumor of human biphenotypic B bone marrow mononuclear leukemia cell MV4-11. A low dose (5 mg/kg) of the compound of the present disclosure shows the same tumor inhibitory effect as that of a high dose (20 mg/kg) of compound A. In the drug withdrawal-rebound assay, the compound of the present disclosure has a more pronounced sustained tumor inhibitory effect than that of compound B at the same dose (5 mg/kg).

Assay Example 7: In Vivo Pharmacokinetic Study in Rats

Assay Purpose:

The purpose of this assay is to evaluate the pharmacokinetic behavior of the compound after single administration by intravenous injection and intragastric gavage, and to investigate the bioavailability after administration by intragastric gavage.

Assay Procedure:

SD male rats aged 7 to 10 weeks were selected. The doses for intravenous and oral administration were 1 mg/kg and 2.5 mg/kg, respectively. The rats were fasted for at least 12 hours before the administration, and resumed feeding 4 hours after the administration. The rats had free access to water throughout the assay period.

On the day of the assay, the animals in the intravenous group were administrated the corresponding compound through a single injection in the tail vein at an administration volume of 5 mL/kg; the oral group were administrated the corresponding compound through a single intragastric gavage at an administration volume of 10 mL/kg. The animals were weighed before administration, and the administration volume was calculated based on the body weight. The time for collecting samples was: 0.083 (the injection group), 0.25, 0.5, 1, 2, 4, 6, 8, 24 h. About 200 μL of whole blood was collected from the jugular vein at each time point to prepare plasma for concentration determination by high-performance liquid chromatography-tandem mass spectrometry (LC-MS/MS). All animals were euthanized by $CO_2$ anesthesia after collecting the PK samples at the last time point. The plasma concentrations were processed by non-compartmental model of WinNonlin™ Version 6.3 (Pharsight, Mountain View, Calif.) pharmacokinetic software, and the pharmacokinetic parameters were calculated by the linear logarithm trapezoidal method.

Assay Results:

The results of in vivo PK property evaluation in rats are shown in Table 7.

TABLE 7

Results of evaluation of in vivo pharmacokinetic properties

| Administration | Parameter | Compound B | Trifluoroacetate salt of compound of formula (I) |
|---|---|---|---|
| Injection (1 mg/kg) | $T_{1/2}$ (hr) | 2.73 | 2.99 |
| | Vdss (L/Kg) | 10.2 | 13.3 |
| | Cl (mL/min/Kg) | 44.0 | 61.2 |
| | $AUC_{0-last}$ (nm · h) | 587 | 457 |
| Oral administration (2.5 mg/kg) | $C_{max}$ (nM) | 29.1 | 40.6 |
| | $T_{max}$ (h) | 6.00 | 8.00 |
| | $AUC_{0-last}$ (nM/hr) | 361 | 510 |
| | F % | 24.6 | 44.7 |

Assay Conclusion

The compound of the present disclosure has excellent oral AUC and bioavailability, and has good pharmacokinetic properties in rats. The compound of the present disclosure has unexpectedly improved PK properties compared to compound B.

Assay Example 8: Assay of Inhibition of Molm-13 Subcutaneous Xenograft Tumor In Vivo Assay Purpose:

The purpose of this assay is to evaluate the pharmacodynamics of the compounds in the NOD/SCID female mice model of human acute myeloma MOLM-13 cell line subcutaneous xenograft.

Assay Procedure:

MOLM-13 cells were cultured in RPMI-1640 medium containing 10% fetal bovine serum. The MOLM-13 cells were collected in the exponential growth phase, and resuspended in PBS to a suitable concentration for subcutaneous tumor inoculation in nude mice.

The assay mice were inoculated with $5 \times 10^6$ MOLM-13 cells resuspended in 0.1 ml of PBS (0.1 ml per mouse) subcutaneously on the right back. Tumor growth was regularly observed. When the tumor grew to an average volume of 98 $mm^3$, the mice were randomly divided into groups and administered according to tumor size and body weight of the mice.

After the start of administration, the body weight and tumor size of the mice were measured three times a week. The formula for calculating the tumor volume is: tumor volume $(mm^3) = \frac{1}{2} \times (a \times b^2)$ (where a represents the long diameter and b represents the short diameter).

Assay Results:
The tumor inhibitory effect of the compounds is shown in Table 8.

TABLE 8

Results of Molm-13 ectopic xenograft assay

| Compound | | Blank | Compound B | Compound of formula (I) | Compound of formula (I) |
|---|---|---|---|---|---|
| Dose(mg/kg) | | 0 | 15 | 15 | 50 |
| Dosing frequency | | Once a day | Once a day | Once a day | Once a day |
| Mode of administration | | oral | oral | oral | oral |
| Average | Day 0 | 98.03 | 98.02 | 98.34 | 98.05 |
| tumor volume | Day 11 | 837.59 | 401.07 | 156.85 | 53.08 |
| (cubic millimeter) | Day 15 | 2322.08 | 566.95 | 223.09 | 0 |
| % Inhibition rate on day 11 | | — | 59 | 92 | 106 |
| % Inhibition rate on day 15 | | — | 79 | 94 | 104 |

ASSAY CONCLUSION

The compound of the present disclosure has a significant inhibitory effect against the growth of human-derived Molm-13 xenograft tumors. The compound of the present disclosure shows better tumor inhibitory effect than that of compound B at the same dose (15 mg/kg). The tumor volume is reduced to zero at a dose of 50 mg/kg.

What is claimed is:

1. A compound represented by formula (I) or a pharmaceutically acceptable salt thereof,

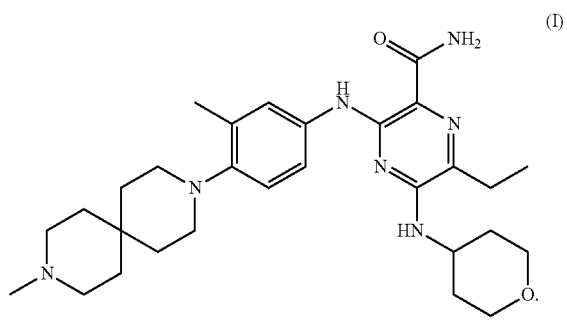 [SMILES: CCc1nc(C(N)=O)c(Nc2ccc(N3CCC4(CCN(C)CC4)CC3)c(C)c2)nc1NC1CCOCC1]

2. A method of treating a cancer in a subject in need thereof, comprising administering to the subject the compound represented by formula (I) or a pharmaceutically acceptable salt thereof according to claim 1, wherein the cancer is acute leukemia.

3. The method according to claim 2, wherein the cancer is acute myeloid leukemia.

4. The compound represented by formula (I) or a pharmaceutically acceptable salt thereof according to claim 1, wherein the pharmaceutically acceptable salt is a trifluoroacetate salt.

5. A method of treating a cancer in a subject in need thereof, comprising administering to the subject the trifluoroacetate salt of the compound represented by formula (I) according to claim 4, wherein the cancer is acute leukemia.

6. The method according to claim 5, wherein the cancer is acute myeloid leukemia.

7. A method of simultaneously inhibiting FLT3 kinase and AXL kinase in a subject in need thereof, comprising administering to the subject the compound represented by formula (I) or a pharmaceutically acceptable salt thereof according to claim 1.

* * * * *